(12) United States Patent
Dumbauld et al.

(10) Patent No.: US 8,133,254 B2
(45) Date of Patent: Mar. 13, 2012

(54) IN VIVO ATTACHABLE AND DETACHABLE END EFFECTOR ASSEMBLY AND LAPAROSCOPIC SURGICAL INSTRUMENT AND METHODS THEREFOR

(75) Inventors: Patrick L. Dumbauld, Lyons, CO (US); Edward Cosgriff, Denver, CO (US)

(73) Assignee: Tyco Healthcare Group LP, Mansfield, MA (US)

( * ) Notice: Subject to any disclaimer, the term of this patent is extended or adjusted under 35 U.S.C. 154(b) by 350 days.

(21) Appl. No.: 12/562,281

(22) Filed: Sep. 18, 2009

(65) Prior Publication Data

US 2011/0071522 A1   Mar. 24, 2011

(51) Int. Cl.
*A61B 18/14* (2006.01)
*A61B 17/28* (2006.01)

(52) U.S. Cl. ............ 606/205; 606/51; 128/898
(58) Field of Classification Search ........ 606/1, 51, 606/52, 205–208; 128/898; 600/104
See application file for complete search history.

(56) References Cited

U.S. PATENT DOCUMENTS

| | | | |
|---|---|---|---|
| 3,862,630 A | 1/1975 | Balamuth | |
| D263,020 S | 2/1982 | Rau, III | |
| 4,597,379 A | 7/1986 | Kihn et al. | |
| D295,893 S | 5/1988 | Sharkany et al. | |
| D295,894 S | 5/1988 | Sharkany et al. | |
| D348,930 S | 7/1994 | Olson | |
| 5,486,185 A * | 1/1996 | Freitas et al. | 606/142 |
| 5,564,615 A | 10/1996 | Bishop et al. | |
| 5,582,617 A | 12/1996 | Klieman et al. | |
| 5,601,224 A | 2/1997 | Bishop et al. | |
| D384,413 S | 9/1997 | Zlock et al. | |
| 5,681,282 A | 10/1997 | Eggers et al. | |
| 5,782,748 A * | 7/1998 | Palmer et al. | 600/104 |
| 5,792,165 A * | 8/1998 | Klieman et al. | 606/170 |
| 5,817,119 A | 10/1998 | Klieman et al. | |
| 5,893,875 A | 4/1999 | Frazier et al. | |
| D424,694 S | 5/2000 | Tetzlaff et al. | |
| D425,201 S | 5/2000 | Tetzlaff et al. | |
| 6,099,550 A | 8/2000 | Yoon | |
| 6,171,316 B1 | 1/2001 | Kovac et al. | |
| 6,190,400 B1 | 2/2001 | Van De Moer et al. | |

(Continued)

FOREIGN PATENT DOCUMENTS

DE   2415263   10/1975

(Continued)

OTHER PUBLICATIONS

U.S. Appl. No. 12/244,873, filed Oct. 3, 2008.

(Continued)

*Primary Examiner* — Michael Peffley (57) ABSTRACT

A method of performing surgery includes the steps of providing a forceps having a housing including a shaft that extends therefrom and at least one handle moveable relative to the housing and providing an end effector assembly configured to selectively engage a distal end of the shaft. The method also includes the steps of inserting the forceps through a first opening formed in a body; inserting the end effector assembly through a second opening formed in the body; engaging the end effector assembly with the distal end of the shaft in vivo; and actuating the end effector assembly by moving the handle relative to the housing. The method may also include the steps of providing a coupling at the distal end of the shaft, and engaging, via the coupling, the distal end of the shaft with the end effector assembly.

18 Claims, 10 Drawing Sheets

U.S. PATENT DOCUMENTS

| | | | |
|---|---|---|---|
| 6,217,615 | B1 | 4/2001 | Sioshansi et al. |
| 6,270,508 | B1 | 8/2001 | Klieman et al. |
| D449,886 | S | 10/2001 | Tetzlaff et al. |
| 6,358,268 | B1 | 3/2002 | Hunt et al. |
| D457,958 | S | 5/2002 | Dycus et al. |
| D457,959 | S | 5/2002 | Tetzlaff et al. |
| 6,402,747 | B1 | 6/2002 | Lindemann et al. |
| 6,409,728 | B1 | 6/2002 | Ehr et al. |
| 6,458,130 | B1 | 10/2002 | Frazier et al. |
| 6,485,489 | B2 | 11/2002 | Teirstein et al. |
| 6,494,877 | B2 * | 12/2002 | Odell et al. ............ 606/1 |
| 6,585,735 | B1 | 7/2003 | Frazier et al. |
| 6,663,639 | B1 | 12/2003 | Laufer et al. |
| 6,663,641 | B1 | 12/2003 | Kovac et al. |
| 6,676,660 | B2 | 1/2004 | Wampler et al. |
| 6,682,528 | B2 | 1/2004 | Frazier et al. |
| 6,726,694 | B2 | 4/2004 | Blatter et al. |
| D493,888 | S | 8/2004 | Reschke |
| 6,773,441 | B1 | 8/2004 | Laufer et al. |
| D496,997 | S | 10/2004 | Dycus et al. |
| D499,181 | S | 11/2004 | Dycus et al. |
| 6,821,285 | B2 | 11/2004 | Laufer et al. |
| 6,835,200 | B2 | 12/2004 | Laufer et al. |
| 6,916,314 | B2 * | 7/2005 | Schneider et al. .......... 606/1 |
| D509,297 | S | 9/2005 | Wells |
| 6,958,070 | B2 | 10/2005 | Witt et al. |
| D525,361 | S | 7/2006 | Hushka |
| D531,311 | S | 10/2006 | Guerra et al. |
| 7,131,970 | B2 | 11/2006 | Moses et al. |
| D533,942 | S | 12/2006 | Kerr et al. |
| 7,153,314 | B2 | 12/2006 | Laufer et al. |
| D535,027 | S | 1/2007 | James et al. |
| 7,160,298 | B2 | 1/2007 | Lawes et al. |
| 7,179,255 | B2 | 2/2007 | Lettice et al. |
| D541,418 | S | 4/2007 | Schechter et al. |
| D541,938 | S | 5/2007 | Kerr et al |
| 7,270,664 | B2 | 9/2007 | Johnson et al. |
| 7,276,068 | B2 | 10/2007 | Johnson et al. |
| 7,318,823 | B2 | 1/2008 | Sharps et al. |
| D564,662 | S | 3/2008 | Moses et al. |
| D567,943 | S | 4/2008 | Moses et al. |
| D575,395 | S | 8/2008 | Hushka |
| D575,401 | S | 8/2008 | Hixson et al. |
| 7,901,398 | B2 * | 3/2011 | Stanczak et al. ............ 606/1 |
| 2002/0107517 | A1 | 8/2002 | Witt et al. |
| 2002/0111624 | A1 | 8/2002 | Witt et al. |
| 2003/0069570 | A1 | 4/2003 | Witzel et al. |
| 2003/0139742 | A1 | 7/2003 | Wampler et al. |
| 2004/0210282 | A1 | 10/2004 | Flock et al. |
| 2004/0267254 | A1 | 12/2004 | Manzo et al. |
| 2005/0004569 | A1 | 1/2005 | Witt et al. |
| 2005/0113826 | A1 | 5/2005 | Johnson et al. |
| 2007/0088356 | A1 | 4/2007 | Moses et al. |
| 2007/0173814 | A1 | 7/2007 | Hixson et al. |
| 2008/0004656 | A1 * | 1/2008 | Livneh ............ 606/205 |
| 2008/0039835 | A1 | 2/2008 | Johnson et al. |
| 2008/0045947 | A1 | 2/2008 | Johnson et al. |
| 2008/0195093 | A1 | 8/2008 | Couture et al. |
| 2008/0249527 | A1 | 10/2008 | Couture |
| 2008/0319442 | A1 | 12/2008 | Unger et al. |
| 2008/0319443 | A1 | 12/2008 | Focht et al. |
| 2009/0012520 | A1 | 1/2009 | Hixson et al. |
| 2009/0182327 | A1 | 7/2009 | Unger |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 20 2007 009317 | 10/2007 |
| DE | 19738457 | 1/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

U.S. Appl. No. 12/246,553, filed Oct. 7, 2008.
U.S. Appl. No. 12/248,104, filed Oct. 9, 2008.
U.S. Appl. No. 12/248,115, filed Oct. 9, 2008.
U.S. Appl. No. 12/249,263, filed Oct. 10, 2008.
U.S. Appl. No. 12/254,123, filed Oct. 20, 2008.
U.S. Appl. No. 12/331,643, filed Dec. 10, 2008.
U.S. Appl. No. 12/336,970, filed Dec. 17, 2008.
U.S. Appl. No. 12/352,942, filed Jan. 13, 2009.
U.S. Appl. No. 12/353,466, filed Jan. 14, 2009.
U.S. Appl. No. 12/353,470, filed Jan. 14, 2009.
U.S. Appl. No. 12/353,474, filed Jan. 14, 2009.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/508,052, filed Jul. 23, 2009.
U.S. Appl. No. 12/535,869, filed Aug. 5, 2009.
U.S. Appl. No. 12/543,831, filed Aug. 19, 2009.
U.S. Appl. No. 12/543,969, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
U.S. Appl. No. 12/619,100, filed Nov. 16, 2009.
U.S. Appl. No. 12/621,056, filed Nov. 18, 2009.
U.S. Appl. No. 12/690,726, filed Jan. 20, 2010.
U.S. Appl. No. 12/692,414, filed Jan. 22, 2010.
U.S. Appl. No. 12/692,810, filed Jan. 25, 2010.

U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/710,033, filed Feb. 22, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967, British Medical Journal Feb. 6, 1976, vol. 1, No. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.

Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner $$I_x = \frac{b \cdot h^3}{12}$$

FIG. 1A v = deflection in y direction v′ = dv/dx = slope of deflection curve $d_b$ = v(L) = deflection at right end of beam $\theta_b$ = v′(L) = angle at right end of beam

FIG. 1B

$0 \leq X \leq A$ :  $v = \dfrac{Px^2}{6EI}(3a - x)$ ;  $v' = \dfrac{Px}{2EI}(2a - x)$ $A \leq X \leq L$ :  $v = \dfrac{Pa^2}{6EI}(3x - a)$ ;  $v' = \dfrac{Pa^2}{6EI}$ $\delta_b = \dfrac{Pa^2}{6EI}(3L - a)$ ;  $\theta_b = \dfrac{Pa^2}{2EI}$

FIG. 1C

$v = \dfrac{M_0 x^2}{2EI}$ ;  $v = \dfrac{M_0 a}{2EI}(2x - a)$ ;  $\delta_b = \dfrac{M_0 a}{6EI}(2L - a)$ $v' = \dfrac{M_0 x}{EI}$ ;  $v' = \dfrac{M_0 a}{EI}$ ;  $\theta_b = \dfrac{M_0 a}{EI}$

IN VIVO ATTACHABLE AND DETACHABLE END EFFECTOR ASSEMBLY AND LAPAROSCOPIC SURGICAL INSTRUMENT AND METHODS THEREFOR

BACKGROUND

1. Technical Field

The present disclosure relates to endoscopic or laparoscopic surgery and more particularly to end effector assemblies for surgical instruments used therein.

2. Description of the Related Art

The trend in surgical procedures is to reduce the invasiveness of the procedure by reducing the size of the surgical incision. More and more frequently, the surgical incision is performed in the navel of the patient. For a laparoscopic surgical instrument, the outer shaft diameter is determined by the inner diameter of the ports (cannulae) with which the instrument will be used. As port size decreases to accommodate the reduced size of the surgical incision, the diameter/cross-sectional area of the end effectors of the surgical instrument must be reduced while the length of the end effectors must also be reduced to provide greater rigidity to reduce the susceptibility of the end effectors to deflection.

The resulting rigidity of the end effectors of the instrument thereby necessitates tight dimensional tolerances and a corresponding increase in material and manufacturing costs to provide the necessary rigidity.

SUMMARY

To advance the state of the art of surgery, the present disclosure relates to a method of performing surgery that includes the steps of providing a forceps having a housing including a shaft that extends therefrom and at least one handle moveable relative to the housing and providing an end effector assembly configured to selectively engage a distal end of the shaft. The method also includes the steps of inserting the forceps through a first opening formed in a body; inserting the end effector assembly through a second opening formed in the body; engaging the end effector assembly with the distal end of the shaft in vivo; and actuating the end effector assembly by moving the handle relative to the housing.

The method may include the step of providing a coupling at the distal end of the shaft, and may further include the step of engaging, via the coupling, the distal end of the shaft with the end effector assembly.

BRIEF DESCRIPTION OF THE DRAWINGS

Various embodiments of the present disclosure are described herein with reference to the drawings wherein.

DETAILED DESCRIPTION

Various embodiments of the present disclosure are described hereinbelow with reference to the accompanying drawings. Well-known functions or constructions are not described in detail to avoid obscuring the present disclosure in unnecessary detail.

The present disclosure relates to a laparoscopic surgical instrument having a mating joint to enable attachment and detachment of a detachable end effector. The detachable end effector may be introduced into the abdominal cavity through a surgical incision such as at the navel while the laparoscopic surgical instrument is introduced, without the detachable end effector, into the abdominal cavity through another surgical incision. Alternatively, the detachable end effector may be introduced through a natural orifice such as the anal canal, while the laparoscopic surgical instrument is introduced, without the detachable end effector, through a surgical incision in the abdominal cavity.

The detachable end effector may be introduced by a second instrument, such as a grasper, which is used to attach or connect the detachable end effector to the mating joint of the instrument.

As compared to conventional laparoscopic surgical instruments, since the detachable end effector is introduced through a natural orifice of the patient, the length and the diameter of the detachable end effector of the laparoscopic surgical instrument according to the embodiments of the present disclosure may be increased.

Removal of the diameter and length constraints of the end effectors of the prior art generally allows for looser tolerances and more cost effective end effector fabrication processes. As the diameter is a significant factor in determining the necessary rigidity of the end effector assembly, a larger-diameter end effector assembly can be a longer end effector assembly because the end effector assembly will be less susceptible to deflection and thus provide a more uniform distribution of sealing pressure to the tissue.

Figure 1A:
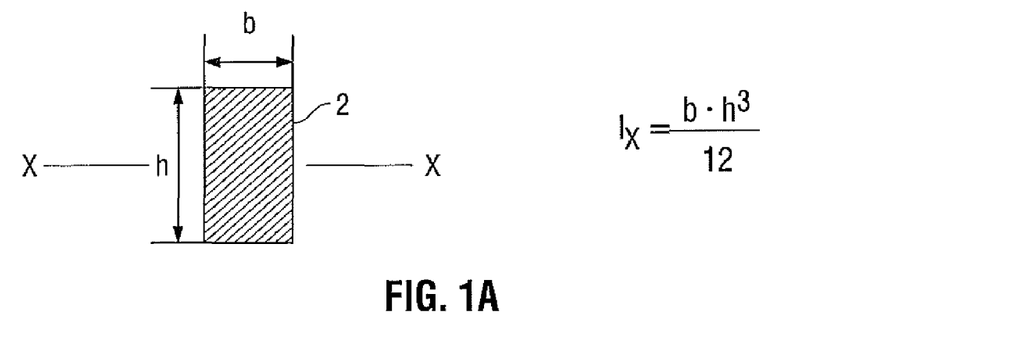
FIG. 1A illustrates a beam having a rectangular cross-section and the corresponding equation and dimensions to calculate the moment of inertia of the beam around a particular axis.
Figure 1B:
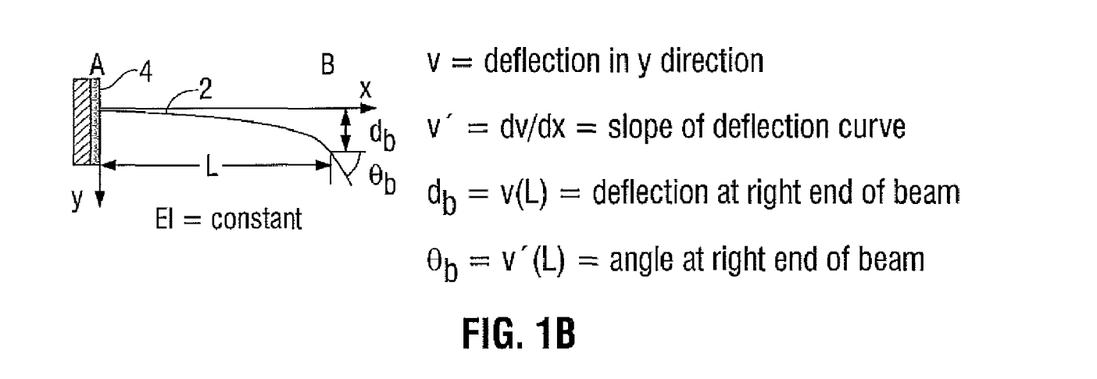
FIG. 1B illustrates a cantilevered beam and the corresponding mathematical factors related to calculating the deflection of the beam along the length of the beam with respect to the anchor point.
Figure 1C:
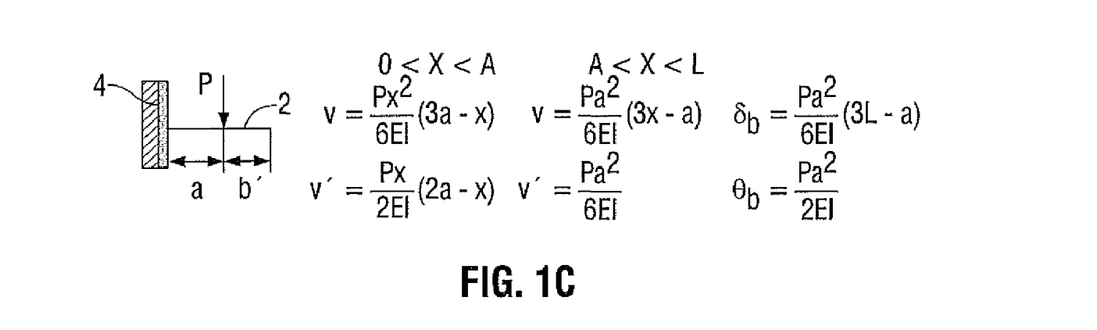
FIG. 1C illustrates the cantilevered beam of FIG. 1B and the equations to calculate the deflection of the beam under a load as a function of the distance along the length of the beam with respect to the anchor point.
Figure 1D:
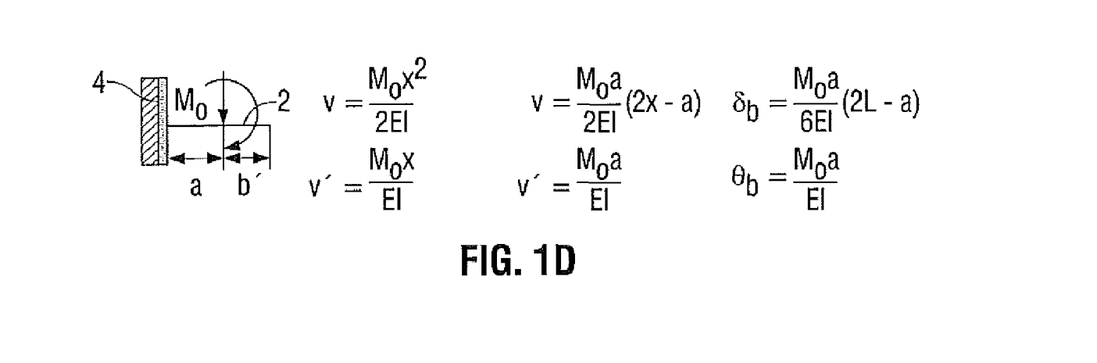
FIG. 1D illustrates the cantilevered beam of FIG. 1B and the equations to calculate the deflection of the beam under a bending moment as a function of the distance along the length of the beam with respect to the anchor point.

As is well-known in the art, deflection of a cantilevered beam, which can approximate the deflection of the end effector assembly with respect to the shaft of the endoscopic instrument, is directly proportional to the distance of the applied load from an anchor point, in this case, the joint between the end effector assembly and the shaft, and inversely proportional to Young's modulus of elasticity E and the moment of inertia I of the end effector assembly, as illustrated in FIGS. 1A-1D. For an assumed rectangular cross-section of the end effector assembly 2 as illustrated in FIG. 1A, since the moment of inertia $I_x$ around the x-axis is proportional to the width b times the cube of the height h, i.e., $h^3$, it can be seen that an increase in height h, while b remains constant, significantly increases the moment of inertia $I_x$. As can then be seen from FIGS. 1B-1C, if the end effector assembly 2 is assumed to be a cantilevered beam anchored at anchor point 4, representing the distal end of a shaft of an endoscopic instrument, the deflection v in the y-direction is directly proportional to the applied load P and the cube of the distance a from the anchor point 4, i.e., $a^3$. Since the load P and the cube of the distance a are independent of the moment of inertia $I_x$, it can then be understood that any increase in moment of inertia $I_x$ (while the other factors remain the same) will reduce the deflection v. FIG. 1D simply illustrates the same effect if one assumes a bending moment $M_0$ around anchor point 4 instead of load P.

Following completion of the surgical procedure, the detachable end effector having an enlarged moment of inertia and rigidity is detached from the mating joint via the second instrument, which may again be introduced through the natural orifice and used to withdraw the detachable end effector from the abdominal cavity while the laparoscopic surgical instrument is withdrawn through the surgical incision.

In the drawings and in the descriptions which follow, the term "proximal", as is traditional, will refer to the end of the forceps 10 which is closer to the user, while the term "distal" will refer to the end which is further from the user. It should be noted that with respect to the end effector assembly 100, reference to proximal end and distal end will be with respect to configuration of the end effector assembly 100 following attachment to the distal end 14 of the shaft 12 and corresponding actual use via the endoscopic bipolar forceps 10 during the surgical procedure, as opposed to the position of the end effector assembly 100 during the attachment process.

Figure 2:
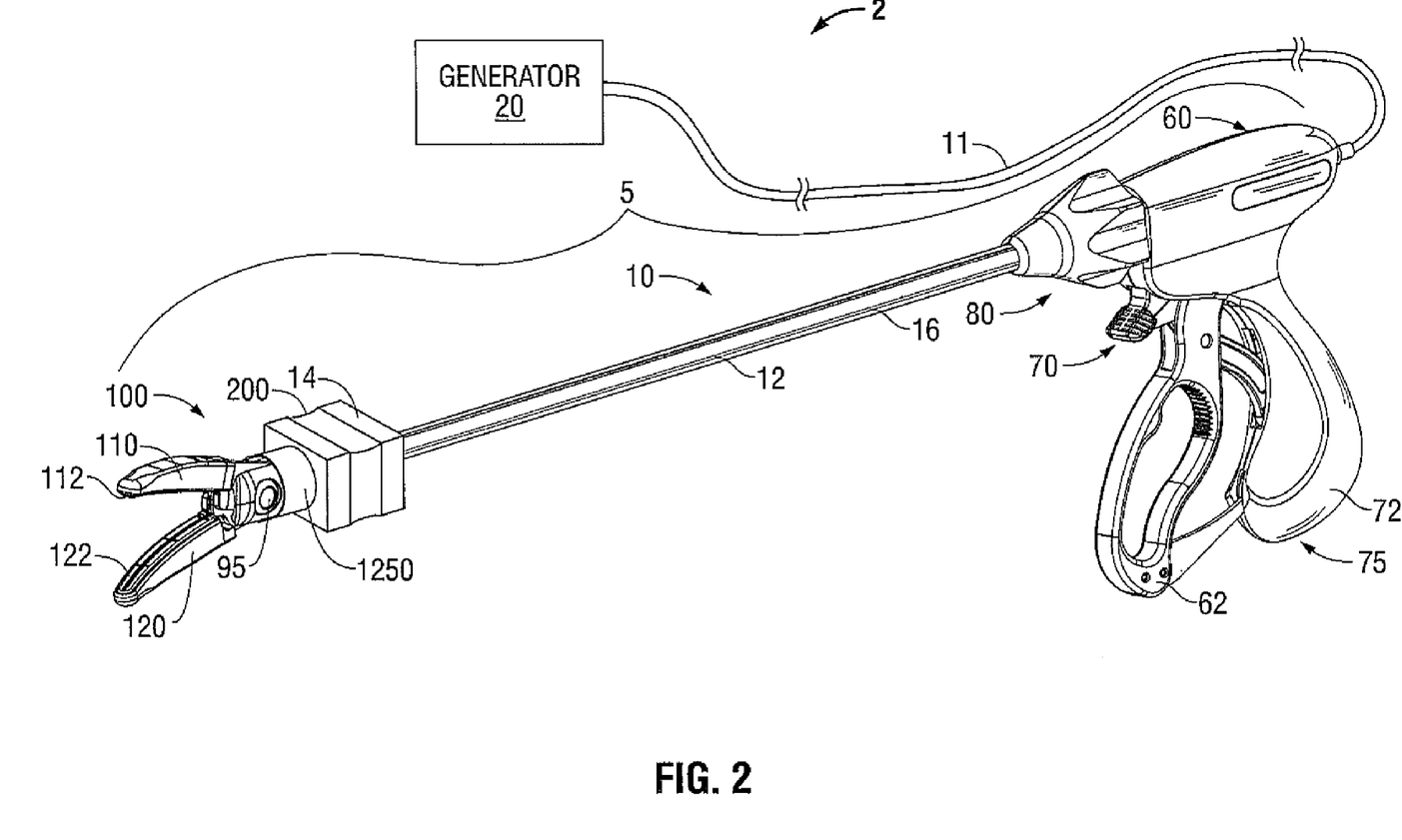
FIG. 2 is a left, perspective view of an endoscopic bipolar forceps showing a housing, a shaft and an in vivo detachable end effector assembly according to one embodiment of the present disclosure.

Referring now to FIG. 2, a tissue sealing system 2 having a combination forceps and in vivo detachable end effector assembly 5 according to the present disclosure is shown. The combination forceps and in vivo detachable end effector assembly 5 includes a forceps 10 coupled to a generator 20. Upon attachment and engagement of end effector assembly 100, as described in more detail below, the combination forceps and in vivo detachable end effector assembly 5 is adapted to seal tissue using electrosurgical energy. The generator 20 may be configured to output various types of electrosurgical energy (e.g., from about 300 MHz to about 10,000 MHz).

The forceps 10 is coupled to the generator 20 via a cable 11 adapted to transmit energy and control signals therebetween. Various embodiments of the forceps 10 utilizing the aforementioned types of energy are discussed in more detail below.

As indicated, the forceps 10 is configured to support an in vivo detachable end effector assembly 100. Forceps 10 typically includes various conventional features (e.g., a housing 60, a handle assembly 75, a rotating assembly 80, a trigger assembly 70) which enable forceps 10 and detachable end effector assembly 100 to mutually cooperate to grasp, seal and, if warranted, divide tissue. Forceps 10 generally includes housing 60 and handle assembly 75, which includes moveable handle 62 and handle 72 that is integral with housing 60. Handle 62 is moveable relative to handle 72 to actuate detachable end effector assembly 100 to grasp and treat tissue. Forceps 10 also includes a shaft 12 that has distal end 14 that mechanically engages detachable end effector assembly 100 and proximal end 16 that mechanically engages housing 60 proximate rotating assembly 80 disposed at the distal end of housing 60. Rotating assembly 80 is mechanically associated with shaft 12. Movement of rotating assembly 80 imparts similar rotational movement to shaft 12 which, in turn, rotates detachable end effector assembly 100.

Figure 3A:
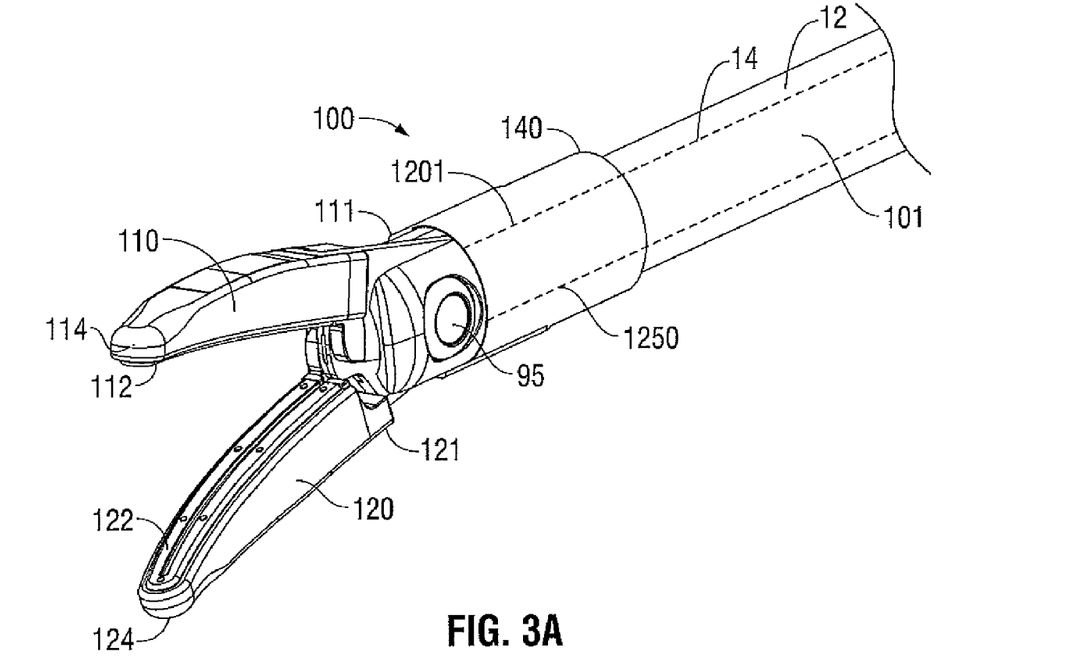
FIG. 3A is an enlarged, left, perspective view of the end effector assembly and shaft of FIG. 1 in which the in vivo detachable end effector assembly is in an open position.
Figure 3B:
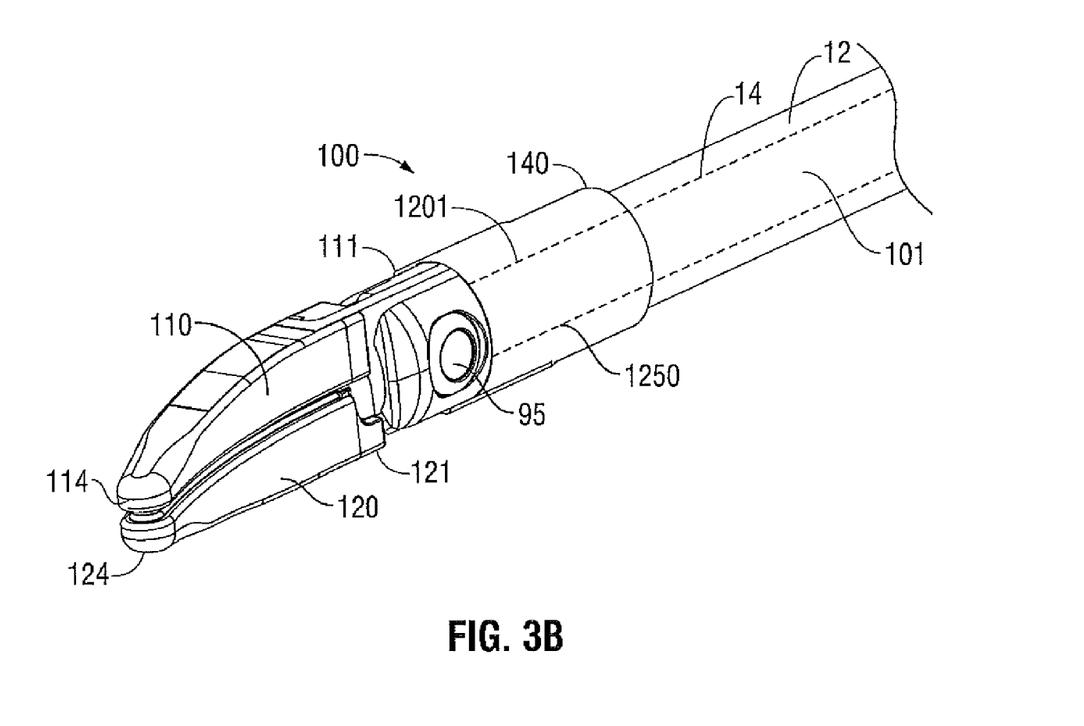
FIG. 3B is a an enlarged, left, perspective view of the end effector assembly and shaft of FIG. 1 in which the in vivo detachable end effector assembly is in a closed position.

Referring also to FIGS. 3A-3B, detachable end effector assembly 100 includes a proximal end 1250 comprising a shaft 1201 at proximal end 1250 that is configured to engage distal end 14 of the shaft 12 of the forceps 10 at interface joint 140. The engagement between the shaft 12 and the shaft 1201 at interface joint 140 enables the attachment and detachment of the end effector assembly 100 with the forceps 10.

Detachable end effector assembly 100 also includes two jaw members 110 and 120 having proximal ends 111, 121 and distal ends 114, 124. Jaw members 110 and 120 are pivotable about a post or pivot pin 95 and are movable from a first position wherein jaw members 110 and 120 are spaced relative to another, to a second position wherein jaw members 110 and 120 are closed and cooperate to grasp tissue therebetween. As discussed in more detail below, the detachable end effector assembly 100 may be adapted for use with various energy sources.

In the illustrated embodiment, the shaft 12 houses a pushrod 101 that is operatively coupled to the movable handle 62 such that when the handle 62 is moved relative to the handle 72 the pushrod 101 moves longitudinally, either proximally or distally within the shaft 12. The pushrod 101 may include one or more pins disposed at the distal end 16 of shaft 12. Each of the jaw members 110 and 120 includes a corresponding slot disposed at the proximal ends thereof that mechanically cooperates with the push pins in a cam-follower mechanical arrangement. Motion of the pushrod 101 causes the pins to slide within respective slots 105 to actuate the jaw members. Other ways of opening/closing the jaws 110 and 120 are contemplated such as any known combinations of mechanical or electro-mechanical arrangement of gears, cams, pulleys, springs and sleeves.

The forceps 10 may also include a trigger assembly 70 that advances a knife 190 disposed within the detachable end effector assembly 100. Once a tissue seal is formed, the user activates the trigger assembly 70 to separate the tissue along the tissue seal.

Each jaw member 110 and 120 also includes a sealing surface 112 and 122, respectively, disposed on an inner-facing surface thereof. Sealing surfaces 112 and 122 cooperate to seal tissue held therebetween upon the application of energy. Sealing surfaces 112 and 122 are connected to generator 20 that communicates energy through the tissue held therebetween.

As best seen in FIG. 2, forceps 10 also includes an electrosurgical cable 11 which connects the forceps 10 to generator 20. Cable 11 is internally divided into cable leads (not shown) which each transmit electrosurgical energy through their respective feed paths through the forceps 10 to the detachable end effector assembly 100.

As mentioned above, detachable end effector assembly 100 is attached at the distal end 14 of shaft 12 and includes a pair of opposing jaw members 110 and 120. As described above, movable handles 62 and 72 mechanically cooperate to impart movement of the jaw members 110 and 120 from an open position, wherein the jaw members 110 and 120 are disposed in spaced relation relative to one another, to a clamping or closed position wherein the jaw members 110 and 120 cooperate to grasp tissue therebetween.

As shown best in FIGS. 3A-3B, 4 and 5, the detachable end effector assembly 100 is designed as a bilateral assembly, i.e., both jaw members 110 and 120 pivot relative to one another about a pivot pin 95 disposed therethrough. The jaw members 110 and 120 are curved to facilitate manipulation of tissue and to provide better "line of sight" for accessing organs and large tissue structures. In other embodiments, the jaw members 110 and 120 may have a straight configuration.

Figure 4:
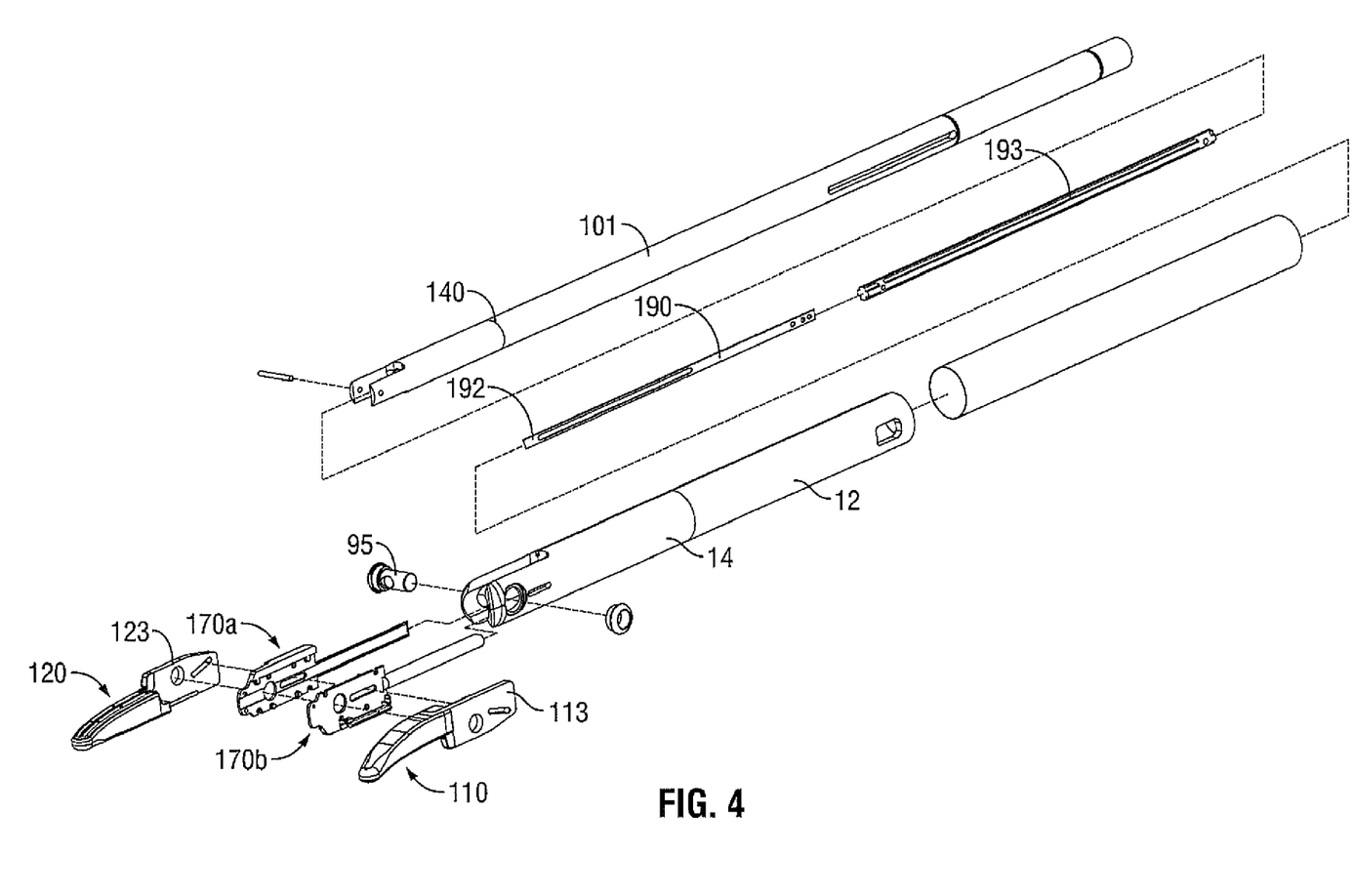
FIG. 4 is a left, perspective, exploded view of the shaft and push rod of the in vivo detachable end effector assembly.
Figure 5:
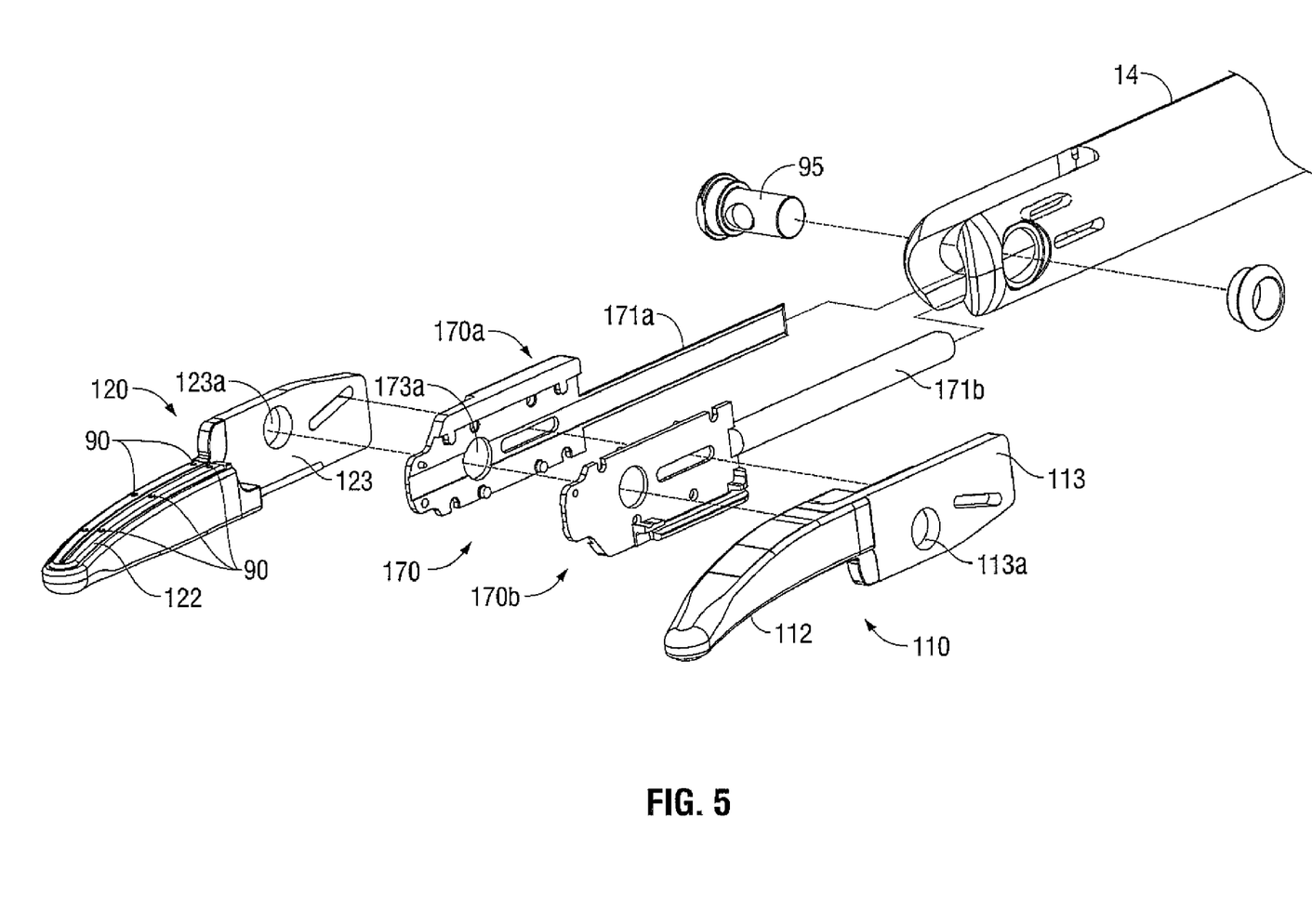
FIG. 5 is a detailed, left, perspective, exploded view of the jaw members of the in vivo detachable end effector assembly.

Push rod 101, which ultimately connects to a drive assembly (not shown), is dimensioned to slidingly receive knife drive rod 193, knife 190 and posts 171a and 171b of halves 170a and 170b of knife guide 170. Push rod 101, in turn, is received within shaft 12. Upon actuation of the drive assembly, the pushrod 101 reciprocates which, in turn, causes the pins to ride within slots to open and close the jaw members 110 and 120 as desired. The jaw members 110 and 120, in turn, pivot about pivot pin 95 disposed through respective pivot holes 113a and 123a disposed within flanges 113 and 123.

Jaw members 110 and 120 are electrically isolated from one another such that electrosurgical energy can be effectively transferred through the tissue to form a tissue seal. Jaw members 110 and 120 are engaged to the end of rotating shaft 12 by pivot pin 95 such that rotation of the rotating assembly 80 correspondingly rotates shaft 12 (along with push rod 101 and knife 190) which, in turn, rotates detachable end effector assembly 100 (See FIG. 2).

Figure 6:
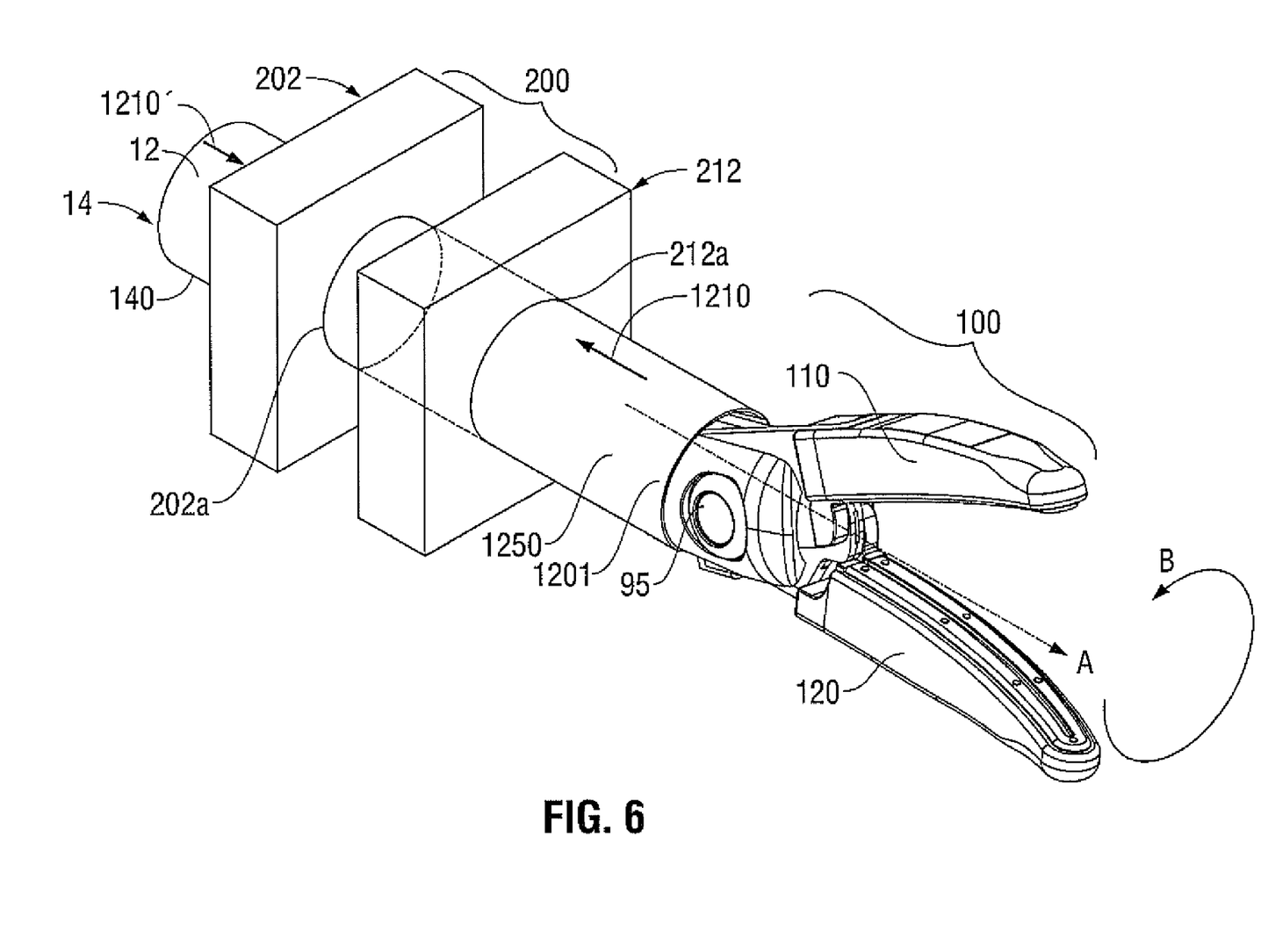
FIG. 6 is a right, perspective view of the in vivo detachable end effector assembly and the shaft generally joined by a coupling according to one embodiment of the present disclosure.

FIG. 6 illustrates the in vivo detachable end effector assembly 100 and the distal end 14 of shaft 12 of the endoscopic surgical instrument or forceps 10 that is generally joined by a coupling 200 according to one embodiment of the present disclosure. The coupling 200 has an orifice 202a at proximal end 202 and an orifice 212a at distal end 212. The orifice 202a at proximal end 202 is configured to receive the distal end 14 of shaft 12 of the endoscopic surgical instrument or forceps 10 while the orifice 212a at distal end 212 is configured to receive proximal end 1250 of the shaft 1201 of the detachable end effector assembly 100. As previously described above with respect to FIGS. 3A and 3B, detachable end effector assembly 100 includes proximal end 1250 comprising shaft 1201 at proximal end 1250 that is configured to engage distal end 14 of the shaft 12 of the forceps 10 at interface joint 140. The engagement between the shaft 12 and the shaft 1201 enables the attachment and detachment of the end effector assembly 100 with the forceps 10 during an in vivo surgical procedure. The installation of the coupling 200 during the in vivo surgical procedure thereby secures the joint 140 and enables the attachment of the end effector assembly 100 to the shaft 12 of the forceps 10. Conversely, release of the coupling 200 upon completion of activities required using the forceps 10 during the in vivo surgical procedure enables the detachment of the end effector assembly 100 from the shaft 12 of the forceps 10. To assist in the installation of the coupling 200, one or more alignment indicators, e.g., an arrow 1210 formed at an appropriate location on the shaft 1201 of the end effector assembly 100 and a corresponding arrow 1210' formed on the shaft 12 of the forceps 10, facilitate engagement of the end effector assembly 100 with the forceps 10 during an in vivo surgical procedure.

Figure 7:
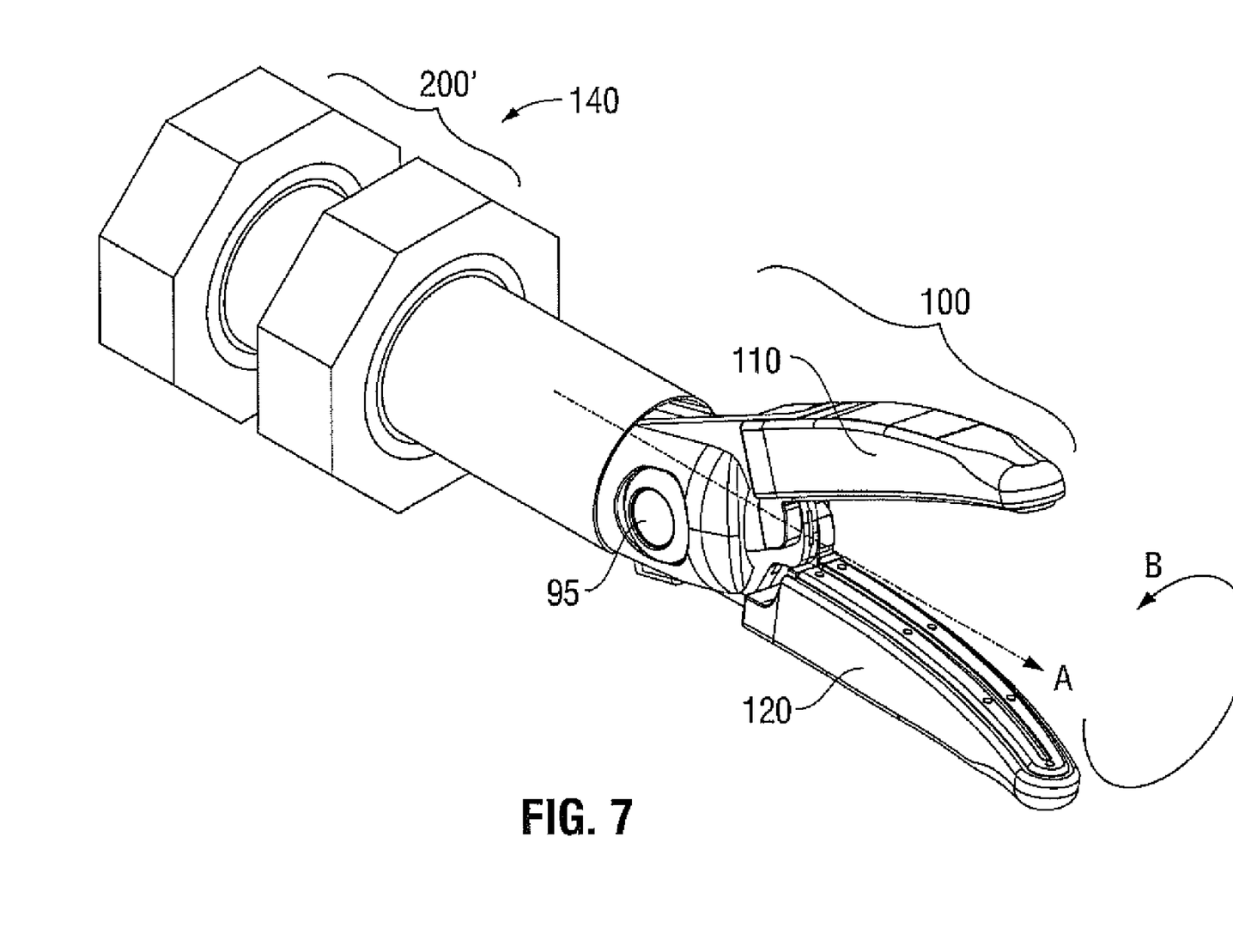
FIG. 7 is a right, perspective view of the in vivo detachable end effector assembly and the shaft joined by a compression coupling according to one embodiment of the present disclosure.

FIG. 7 illustrates the in vivo detachable end effector assembly 100 and the shaft 12 of forceps 10 joined at interface joint 140 by an example coupling, e.g., a compression coupling 200' that may have a compression fitting at one or both ends or a compression fitting at one end and another type of fitting such as a screw threaded fitting at the other end, according to one embodiment of the present disclosure. Numerous other suitable couplings may be employed to perform the joining of the end effector assembly 100 and the shaft 12, including, but not limited to, Luer lock fittings, snap-fit coupling, ball and socket fittings and the like.

The shaft 12 and the end effector assembly 100 are configured such that engagement of the end effector assembly 100 with the distal end 14 of the shaft 12 establishes electrical communication between the forceps 10 and the tissue sealing surface 112 and/or 122 of the end effector assembly 100.

As also described above previously, the distal end 14 of the shaft 12 is configured to interface with coupling 200. The coupling 200 is configured to interface with the end effector assembly 100. The end effector assembly 100 is configured to detachably engage and disengage from the distal end 14 of the shaft 12 via engagement of the end effector assembly 100 with the coupling 200.

The shaft 12 and the end effector assembly 100 are configured such that engagement of the end effector assembly 100 with the distal end 14 of the shaft 12 via the coupling 200 establishes electrical communication between the forceps 10 and the end effector assembly 100.

To accomplish the intended purpose of the combination forceps and in vivo detachable end effector assembly 5 (see FIG. 2), the end effector assembly 100 may be configured to vary the ratio between the moment of inertia of the cross-section of the end effector assembly and the moment of inertia of the cross-section of the shaft 12 depending on any particular surgical purpose.

In addition, coupling 200 may be configured to selectively engage a first end effector assembly having a cross-sectional moment of inertia value and a second end effector assembly having a cross-sectional moment of inertia value that differs from the cross-sectional moment of inertia value of the first end effector assembly. That is, the coupling may be a universal type coupling configured to selectively engage end effector assemblies of different or various sizes.

Figure 8:
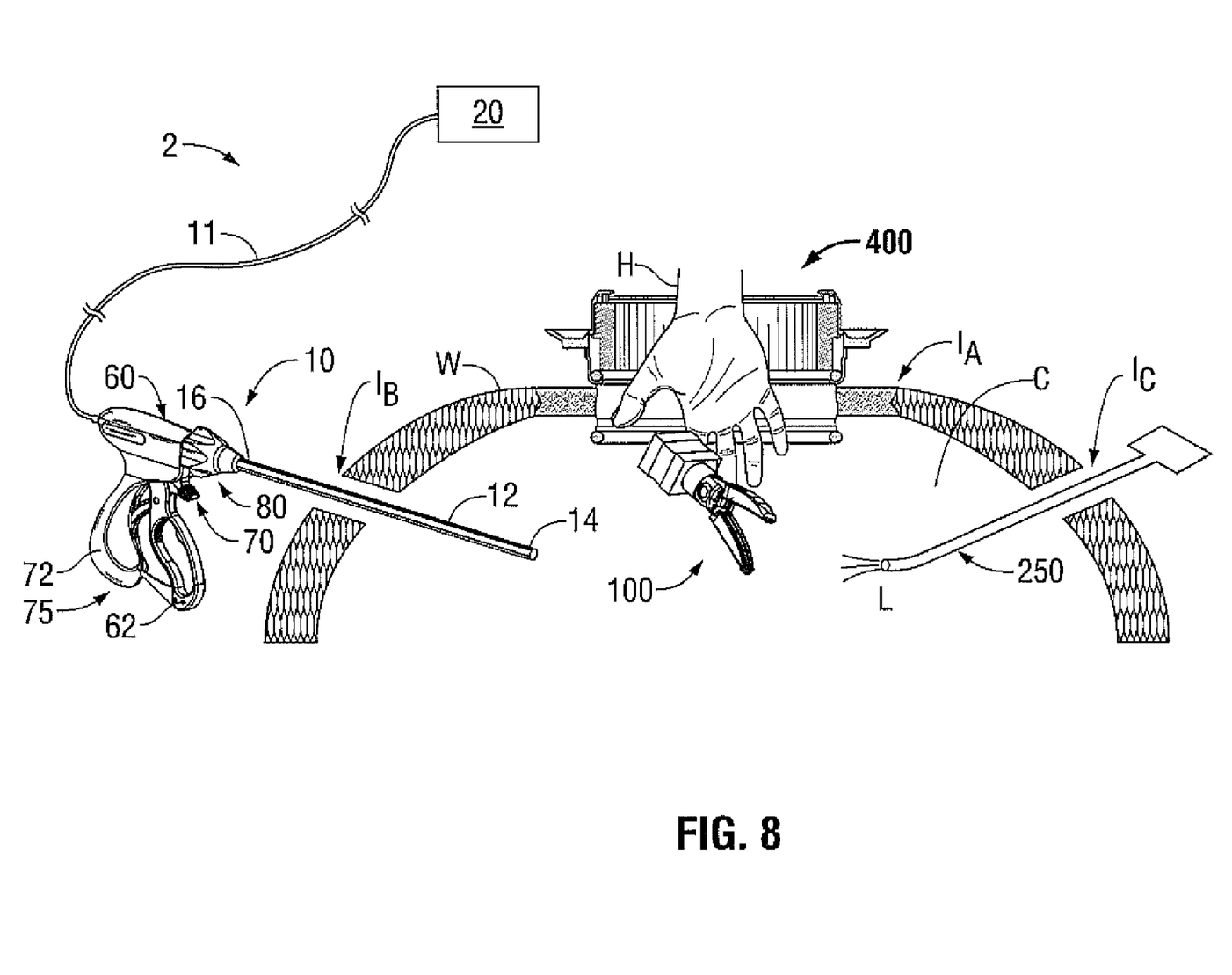
FIG. 8 is a simplified view of an abdominal cavity in a subject illustrating an in vivo method of attaching a detachable end effector assembly to an endoscopic surgical instrument during a laparoscopic procedure according to one embodiment of the present disclosure.
Figure 9:
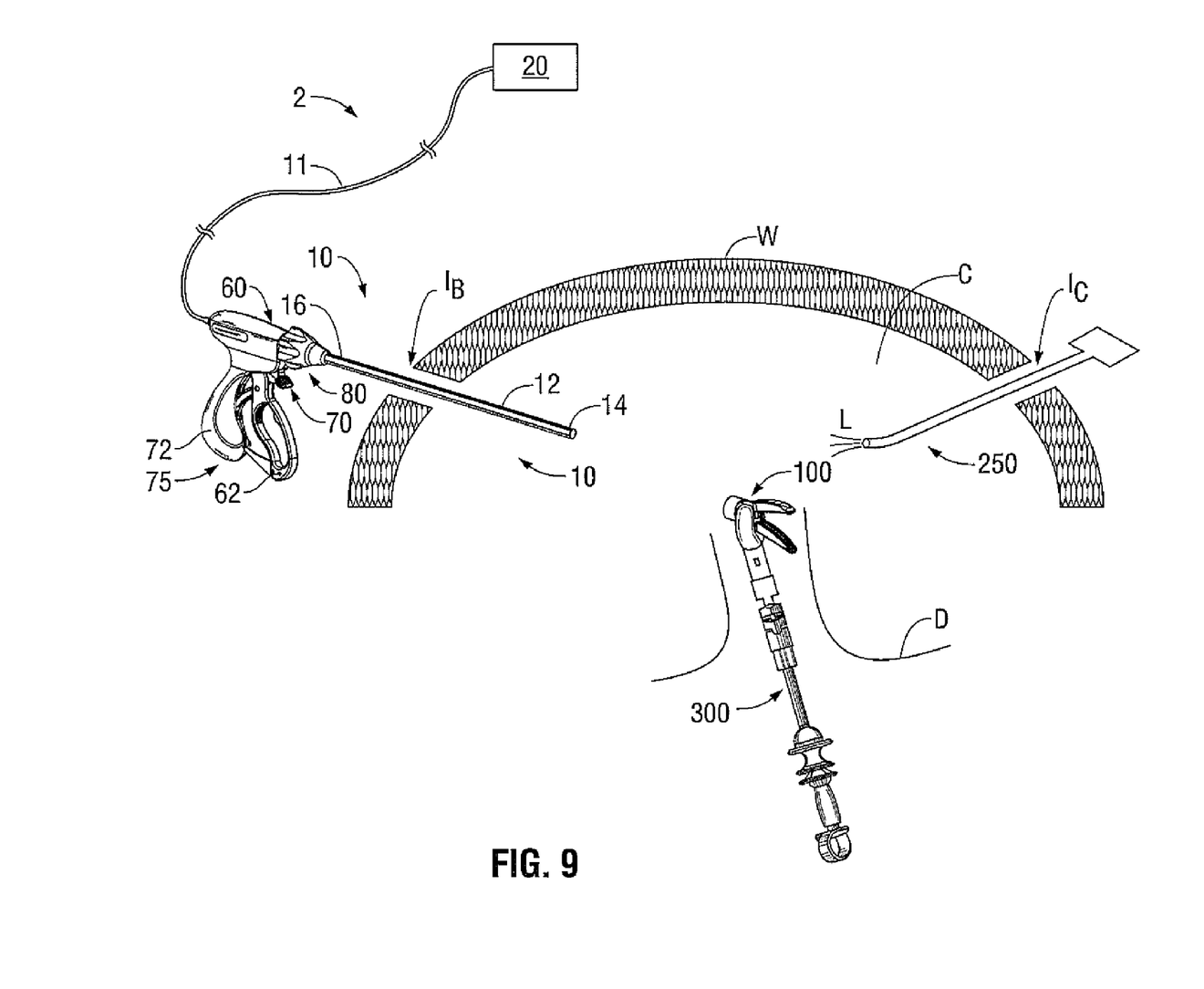
FIG. 9 is a simplified view of an abdominal cavity in a subject illustrating an in vivo method of attaching, via a grasping device, a detachable end effector assembly to an endoscopic surgical instrument during a laparoscopic procedure according to another embodiment of the present disclosure.
Figure 10:
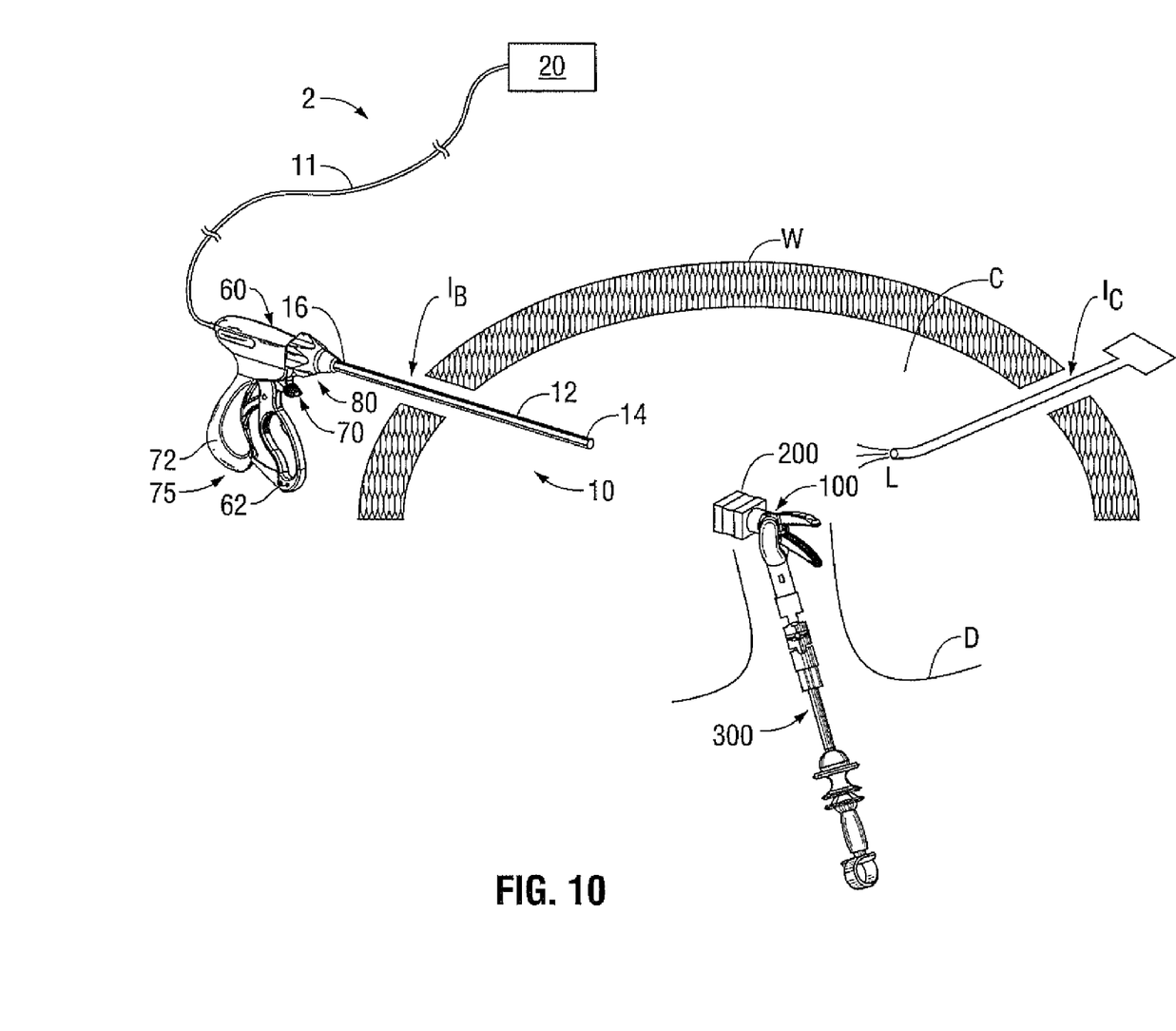
FIG. 10 is a simplified view of an abdominal cavity in a subject illustrating an in vivo method of attaching a detachable end effector assembly to an endoscopic surgical instrument during a laparoscopic procedure via a coupling that is configured to interface with the end effector assembly and the endoscopic surgical instrument according to still another embodiment of the present disclosure.

FIGS. 8-10 illustrate simplified views of portions of the in vivo method of attaching the detachable end effector assembly 100 to the forceps 10 to form the combination forceps and end effector assembly 5 (see FIG. 2) for use during the surgical procedure to seal and cut tissue.

More particularly, FIG. 8 is a simplified view of an abdominal cavity C in a subject illustrating the in vivo method of attaching detachable end effector assembly 100 to forceps 10 during a laparoscopic procedure according to one embodiment of the present disclosure. A surgical hand access apparatus 400 is shown installed within an opening or surgical incision $I_A$ in abdominal wall W located at a position such as at the navel of the subject as shown. Such a surgical hand access apparatus and the method of installation are described in commonly-owned U.S. Patent Application Publication US 2006/0229501 A1, by Jensen et al., entitled "SURGICAL HAND ACCESS APPARATUS". The hand H of a surgeon is illustrated grasping the in vivo detachable end effector assembly 100 and inserting or positioning the end effector assembly 100 through the incision $I_A$ and into the abdominal cavity C. The end effector assembly 100 is grasped and oriented in a position to facilitate attachment and engagement of the end effector assembly 100 with the forceps 10.

The forceps 10 is provided and inserted, minus the detachable end effector assembly 100, through another opening or incision $I_B$ in the body that allows the surgeon to position the distal end 14 of the shaft 12 such that upon attachment and engagement of the end effector assembly 100 to the shaft 12, the resulting combination forceps and end effector assembly 5 (see FIG. 2) is advantageously positioned to perform the desired surgical procedure.

Although not shown, the method further includes the step of engaging the end effector assembly 100 with the distal end 14 of the shaft 12. The step of engaging the end effector assembly 100 with the distal end 14 of the shaft 12 enables establishment of electrical communication between the forceps 10 and the tissue sealing surface 112 and/or 122 of jaw members 110 and/or 120 of the end effector assembly 100.

When at least one jaw member, e.g., lower jaw member 120, of the end effector assembly 100 further includes a mechanical cutting element, e.g., knife blade 190, the step of engaging the end effector assembly 100 with the distal end 14 of the shaft 12 also enables establishment of mechanical communication between the forceps 10 and the mechanical cutting element of the jaw member 120 to enable mechanical cutting of tissue.

As described above to assist in the installation of the coupling 200, the method may include providing one or more alignment indicators, e.g., arrow 1210 formed at an appropriate location on the shaft 1201 of the end effector assembly 100 and/or corresponding arrow 1210' formed on the shaft 12 of the forceps 10, to facilitate engagement of the end effector assembly 100 with the forceps 10 during an in vivo surgical procedure. The step of aligning the end effector assembly 100 with the forceps 10 may include rotating the end effector assembly 100, in the direction indicated by arrow B around longitudinal axis A of the end effector assembly 100, and also translating the end effector assembly 100 in the direction of the longitudinal axis A, as illustrated in FIGS. 6 and 7.

To further assist the surgeon in implementing the attachment and engagement of the end effector assembly 100 to the shaft 12 and in implementing the surgical procedure, an endoscopic camera 250 may be positioned and inserted through the abdominal wall W into the abdominal cavity C through another opening or incision $I_C$ in the body at an opposite side of the abdominal wall W to facilitate transmission of light L towards the end effector assembly 100 and the distal end 14 of the shaft 12 and to facilitate reception of cinematic images.

FIG. 9 is a simplified view of the abdominal cavity C in a subject illustrating an in vivo method of attaching, via a grasping device, the detachable end effector assembly 100 to the forceps 10 during a laparoscopic procedure according to another embodiment of the present disclosure. A grasping device 300, such the endoscopic surgical device having an articulating handle assembly that is disclosed in commonly-owned U.S. patent application Ser. No. 12/193,864 by De Santis et al., filed on Aug. 19, 2008, entitled "ENDOSCOPIC SURGICAL DEVICE", the entire contents of which are hereby incorporated by reference herein, is positioned and inserted through an opening in the body such as a natural orifice D, Again, the end effector assembly 100 is grasped and oriented in a position to facilitate attachment and engagement of the end effector assembly 100 with the forceps 10.

In a similar manner as described above with respect to FIG. 8, the forceps 10 is provided and inserted, minus the detachable end effector assembly 100, through opening or incision $I_B$ in the body that allows the surgeon to position the distal end 14 of the shaft 12 such that upon attachment and engagement of the end effector assembly 100 to the shaft 12, the resulting combination forceps and end effector assembly 5 (see FIG. 2) is advantageously positioned to perform the desired surgical procedure.

Again, although not shown, the method may further include the step of engaging the end effector assembly 100 with the distal end 14 of the shaft 12. The step of engaging the end effector assembly 100 with the distal end 14 of the shaft 12 enables establishment of electrical communication between the forceps 10 and the end effector assembly 100.

In a similar manner, when at least one jaw member, e.g., lower jaw member 120, of the end effector assembly 100 further includes a mechanical cutting element, e.g., knife blade 190, the step of engaging the end effector assembly 100 with the distal end 14 of the shaft 12 also enables establishment of mechanical communication between the forceps 10 and the mechanical cutting element (knife blade 190) of the jaw member 120 to enable mechanical cutting of tissue.

FIG. 10 is a simplified view of the adominal cavity C in a subject illustrating an alternative in viva method of attaching the detachable end effector assembly 100 to forceps 10 during a laparoscopic procedure, as compared to the in vivo method described above with respect to FIG. 9, via the coupling 200 that is configured to interface with the end effector assembly 100 and the forceps 10, according to still another embodiment of the present disclosure.

As described previously above with respect to FIGS. 6 and 7, the end effector assembly 100 and the distal end 14 of the shaft 12 of the forceps 10 are configured to interface with the coupling 200. As can be appreciated, the previous steps of implementing the method of engaging the forceps 10 with the end effector assembly 100 described above with respect to FIG. 9 are each implemented by interfacing the coupling 200 with the end effector assembly 100 and with the distal end 14 of the shaft 12.

The methods described above with respect to FIGS. 8-10 may be implemented wherein forceps 10 includes trigger assembly 70 (that includes a trigger—see FIG. 2) operably coupled to the housing 60 and the end effector assembly 100 includes a knife 192 (see FIG. 4) and the method includes the step of actuating the trigger 70 to advance the knife 192 to separate tissue disposed in the end effector assembly 100.

Additionally, the method may be implemented by providing coupling 200 configured to selectively engage a first end effector assembly having a cross-sectional moment of inertia value and a second end effector assembly having a cross-sectional moment of inertia value that differs from the cross-sectional moment of inertia value of the first end effector assembly depending on a surgical need. That is, as described previously, the coupling 200 may be a universal type coupling configured to selectively engage end effector assemblies of different or various sizes depending on the requirements for a particular surgical procedure or need.

Actuation of the handles 62 and 72 closes the jaw members 110 and 120 about tissue with a pre-determinable and consistent closure pressure to effect a tissue seal. Closure pressures for sealing large tissue structures fall within the range of about 3 kg/cm$^2$ to about 16 kg/cm$^2$.

Stop members 90 which extend from the sealing surface 122 provide a consistent and accurate gap distance "G" (not shown) between the electrically conductive sealing surfaces 112 and in the range from about 0.001 inches (about 0.0254 millimeters) to about 0.006 inches (about 0.1524 millimeters) which is also effective for sealing tissue.

After the tissue is grasped between jaw members 110 and 120, the forceps 10 is ready for selective application of electrosurgical energy and subsequent separation of the tissue. By controlling the intensity, frequency and duration of the electrosurgical energy and pressure applied to the tissue, the user can effectively seal tissue.

Referring to FIG. 2, it can be appreciated from the foregoing that the embodiments of the present disclosure may include a kit for an in vivo surgical procedure that includes forceps 10 having housing 60 including shaft 12 that extends therefrom and at least one handle 62 that is movable relative to the housing 60. The kit also includes the selectively engageable end effector assembly 100 that is configured to selectively engage the distal end 14 of the shaft 12. The kit may further include coupling 200 that is configured to facilitate engagement of the end effector assembly 100 to the forceps 10.

The state of the art of endoscopic surgery is advanced by the embodiments of the present disclosure, since the embodiments of the present disclosure enable removing the diameter and length constraints of the end effectors of the prior art to generally allow for looser tolerances and more cost effective end effector fabrication processes. As described above, the diameter is a significant factor in determining the necessary rigidity of the end effector assembly, so that a larger-diameter end effector assembly can be a longer end effector assembly because the end effector assembly will be less susceptible to deflection and thus will provide a more uniform distribution of sealing pressure to the tissue.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of performing surgery, comprising the steps of:
    providing a forceps having a housing including a shaft that extends therefrom and at least one handle moveable relative to the housing;
    providing an end effector assembly configured to selectively engage a distal end of the shaft;
    inserting the forceps through a first opening formed in a body;
    inserting the end effector assembly through a second opening formed in the body;
    engaging the end effector assembly with the distal end of the shaft in vivo; and
    actuating the end effector assembly by moving the handle relative to the housing.

2. A method of performing surgery according to claim 1, wherein the step of engaging the end effector with the shaft establishes an electro-mechanical connection for electrosurgically treating tissue.

3. A method of performing surgery according to claim 1, wherein the end effector assembly is adapted to connect to an electrosurgical energy source and the method further includes the step of activating the end effector assembly, via the electrosurgical energy source, to treat tissue.

4. A method of performing surgery according to claim 1, wherein the step of inserting the forceps through a first opening formed in a body is performed by inserting the forceps through a natural body orifice.

5. A method of performing surgery according to claim 1, wherein the step of inserting the end effector assembly through a second opening formed in the body is performed by inserting the end effector assembly through a natural body orifice.

6. A method of performing surgery according to claim 1, wherein the method includes the step of inserting a camera through a third opening in the body.

7. A method of performing surgery according to claim 6, further comprising the step of visualizing, via the camera, engagement of the end effector assembly with the distal end of the shaft.

8. A method of performing surgery according to claim 1, further comprising the step of inserting a grasping device through a third opening in the body.

9. A method of performing surgery according to claim 8, wherein the step of inserting the grasping device through a third opening in the body is performed by grasping the end effector assembly via the grasping device and inserting the end effector assembly through a third opening in the body.

10. A method of performing surgery according to claim 9, further comprising the step of engaging the end effector assembly with the distal end of the shaft.

11. A method of performing surgery according to claim 1, further comprising the step of providing a coupling at the distal end of the shaft.

12. A method of performing surgery according to claim 11, further comprising the step of engaging, via the coupling, the distal end of the shaft with the end effector assembly.

13. A method of performing surgery according to claim 11, wherein the step of providing a coupling at the distal end of the shaft is performed by providing at least one of a leer-lock coupling, a threaded coupling, a compression coupling, a snap-fit coupling, a slide-fit coupling and a magnetic coupling.

14. A method of performing surgery according to claim 1, wherein the forceps includes a trigger operably coupled to the housing and the end effector assembly includes a knife and the method includes the step of actuating the trigger to advance the knife to separate tissue disposed in the end effector assembly.

15. A method of performing surgery according to claim 1, further comprising the step of providing an alignment indicator to at least one of the forceps and the end effector assembly to facilitate engagement between the forceps and the end effector assembly.

16. A method of performing surgery according to claim 15, further comprising the step of aligning the forceps and the end effector assembly.

17. A method of performing surgery according to claim 16, further comprising the step of engaging the forceps and the end effector assembly.

18. A method of performing surgery according to claim 11, wherein the step of providing a coupling at the distal end of the shaft is performed by providing a coupling configured to selectively engage a first end effector assembly having a cross-sectional moment of inertia and a second end effector assembly having a cross-sectional moment of inertia that differs from the cross-sectional moment of inertia of the first end effector assembly.

* * * * *